(12) United States Patent
Boverman et al.

(10) Patent No.: US 10,357,177 B2
(45) Date of Patent: Jul. 23, 2019

(54) SYSTEMS AND METHODS FOR ELECTRICAL IMPEDANCE IMAGING

(71) Applicant: General Electric Company, Schenectady, NY (US)

(72) Inventors: Gregory Boverman, Saratoga Springs, NY (US); Jeffrey Michael Ashe, Gloversville, NY (US); Bruce Courtney Campbell Amm, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 846 days.

(21) Appl. No.: 14/105,203

(22) Filed: Dec. 13, 2013

(65) Prior Publication Data

US 2015/0164369 A1  Jun. 18, 2015

(51) Int. Cl.
| | | |
|---|---|---|
| *A61B 5/00* | (2006.01) | |
| *A61B 5/053* | (2006.01) | |
| *G01R 27/02* | (2006.01) | |
| *G01R 27/16* | (2006.01) | |
| *G01R 27/26* | (2006.01) | |
| *A61B 5/0424* | (2006.01) | |

(52) U.S. Cl.
CPC .......... *A61B 5/0536* (2013.01); *A61B 5/0531* (2013.01); *A61B 5/6885* (2013.01); *A61B 5/0424* (2013.01); *A61B 5/6843* (2013.01); *G01R 27/02* (2013.01); *G01R 27/16* (2013.01); *G01R 27/26* (2013.01)

(58) Field of Classification Search
CPC ..... A61B 5/0536; A61B 5/6885; A61B 5/053; A61B 5/0531; A61B 5/6843; G01R 27/02; G01R 27/16; G01R 27/26
See application file for complete search history.

(56) References Cited

U.S. PATENT DOCUMENTS

| | | | |
|---|---|---|---|
| 4,920,490 A | 4/1990 | Isaacson | |
| 5,272,624 A | 12/1993 | Gisser et al. | |
| 5,381,333 A | * 1/1995 | Isaacson | .............. A61B 5/0536 |
| | | | 128/922 |

(Continued)

OTHER PUBLICATIONS

Vauhkonen et al., "A Kalman filter approach to track fast impedance changes in electrical impedance tomography", Biomedical Engineering, IEEE Transactions on, vol. 45, Issue 4, Apr. 1998, pp. 486-493.

(Continued)

*Primary Examiner* — Devin B Henson (57) ABSTRACT

A method and system for performing electrical impedance imaging of a subject of interest using a plurality of electrodes is provided. The method includes applying one or more determined current patterns to one or more electrodes of the plurality of electrodes. Further, the method includes determining a resultant voltage at at least one electrode of the one or more electrodes in response to the one or more determined current patterns. Moreover, the method includes estimating a change in a contact impedance for the at least one electrode of the one or more electrodes. Additionally, the method includes calculating a compensated voltage for the at least one electrode based on an estimated change in a corresponding contact impedance of the at least one electrode.

20 Claims, 9 Drawing Sheets

(56) References Cited

U.S. PATENT DOCUMENTS

| | | | | |
|---|---|---|---|---|
| 5,501,230 | A | * | 3/1996 | Laribiere .............. A61B 5/0424 600/508 |
| 5,588,429 | A | | 12/1996 | Isaacson et al. |
| 5,749,369 | A | * | 5/1998 | Rabinovich .......... A61B 5/0535 600/372 |
| 6,236,886 | B1 | * | 5/2001 | Cherepenin .......... A61B 5/0536 600/547 |
| 6,501,984 | B1 | | 12/2002 | Church et al. |
| 8,088,076 | B2 | | 1/2012 | Pomfrett et al. |
| 8,264,246 | B2 | | 9/2012 | Mahalingam et al. |
| 8,352,016 | B2 | | 1/2013 | Tanaka |
| 2006/0020218 | A1 | * | 1/2006 | Freeman ................. A61B 5/04 600/509 |
| 2012/0166127 | A1 | * | 6/2012 | Ross .................... A61B 5/0536 702/104 |
| 2013/0002264 | A1 | * | 1/2013 | Garber ................. A61B 5/0536 324/600 |
| 2014/0247058 | A1 | * | 9/2014 | Mortara ............... A61B 5/0424 324/601 |
| 2016/0113540 | A1 | * | 4/2016 | Chi ...................... A61B 5/6843 600/509 |

OTHER PUBLICATIONS

Hua et al., "Using compound electrodes in electrical impedance tomography", Biomedical Engineering, IEEE Transactions on, vol. 40, Issue 1, 1993, pp. 29-34.

Boverman et al., "The complete electrode model for imaging and electrode contact compensation in electrical impedance tomography", Engineering in Medicine and Biology Society, 2007. EMBS 2007. 29th Annual International Conference of the IEEE, Aug. 2007, pp. 3462-3465.

Boverman et al., "Methods for compensating for variable electrode contact in EIT", IEEE Transactions on Biomedical Engineering, vol. 56, No. 12, Dec. 2009.

* cited by examiner

SYSTEMS AND METHODS FOR ELECTRICAL IMPEDANCE IMAGING

BACKGROUND

The embodiments of the present specification relate to impedance imaging, and more particularly to electrical impedance imaging.

In electrical impedance tomography, currents are injected through electrodes and corresponding voltages are measured at the electrodes to determine a resistivity distribution in an internal medium of a subject of interest. The measured voltages are representative of voltage drops along a current pathway. Also, the measured voltages may entail both an internal impedance of the internal medium and a contact impedance at an interface of an electrode and the subject of interest. It may be noted that the contact impedance exists at the interface between the electrode and a surface of the subject of interest. In one example, in the case of the electrode-skin contact, the contact impedance exists at an electrode-skin interface and may be referred to as electrode-skin contact impedance. In another example, in case of saline phantom studies, the contact impedance may exist in the form of electrode-electrolyte impedance. Moreover, an internal current density distribution in the subject of interest may be influenced by the contact impedance, thereby adversely affecting the impedance imaging.

Additionally, a voltage drop across the contact impedance is relatively large as compared to voltage drops across the internal impedance. Also, the electrode-skin contact impedance and/or the electrode-electrolyte impedance may change over time as the interface absorbs or desorbs fluids and/or ions.

BRIEF DESCRIPTION

In one aspect, a method for electrical impedance imaging of a subject of interest using a plurality of electrodes is provided. The method includes applying one or more determined current patterns to one or more electrodes of the plurality of electrodes. Further, the method includes determining a resultant voltage at at least one electrode of the one or more electrodes in response to the one or more determined current patterns. Moreover, the method includes estimating a change in a contact impedance for at least one electrode of the one or more electrodes. Additionally, the method includes calculating a compensated voltage for at least one of the one or more electrodes based on the estimated change in a corresponding contact impedance of an electrode of the one or more electrodes.

In another aspect, a method for imaging a subject of interest using electrical impedance imaging includes:
a) applying one or more determined current patterns to two or more electrodes of a plurality of electrodes,
b) determining one or more resultant voltages at the one or more electrodes at two or more instants in time,
c) estimating changes in contact impedances for the two or more electrodes at the two or more instants in time,
d) if there is a change in a contact impedance for a given electrode between the two or more instants in time, calculating a compensated voltage for the given electrode based on the change in the contact impedance for the given electrode, and
e) reconstructing an image based on the compensated voltage for each of the two or more electrodes.

In yet another aspect, an electrical impedance imaging system for imaging a subject of interest includes a plurality of electrodes configured to be disposed on the subject of interest. The system further includes a plurality of electrical channels, where each electrical channel of the plurality of electrical channels is configured to be operatively coupled to a corresponding electrode of the plurality of electrodes. Furthermore, the system includes a processor unit. The processor unit includes a physiological parameter extraction module, and a contact impedance compensator module. Additionally, the contact impedance compensator module is configured to provide compensation at least in part for a change in contact impedance of one or more electrodes of the plurality of electrodes.

DRAWINGS

These and other features and aspects of embodiments of the invention will become better understood when the following detailed description is read with reference to the accompanying drawings in which like characters represent like parts throughout the drawings, wherein.

DETAILED DESCRIPTION

To the extent that the figures illustrate diagrams of the functional blocks of various embodiments, the functional blocks are not necessarily indicative of the division between hardware circuitry. Thus, for example, one or more of the functional blocks (e.g., a processor unit, an electrode current source, an excitation source, or a contact impedance compensator module) may be implemented in a single piece of hardware or multiple pieces of hardware. Further, it should be understood that the various embodiments are not limited to the arrangements and instrumentalities shown in the drawings.

As used herein, an element or step recited in the singular and proceeded with the word "a" or "an" should be understood as not excluding plural of elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It should be noted that although described primarily with respect to monitoring a current in a human subject, the electrical impedance imaging may be used in other applications, such as, but not limited to, defect detection, geological imaging, and process monitoring. Further, it should be noted that the electrical impedance imaging system may be an electrical impedance spectroscopy (EIS) system, an electrical impedance tomography (EIT), or an electrical capacitance tomography (ECT) system. Additionally, compensation for a change in a contact impedance of one or more electrodes of a plurality of electrodes may be implemented in connection with any system that is capable of measuring the contact impedance of an object (e.g., a portion of a patient). In some embodiments, biological systems may include thorax of a human body. Further, while the present specification is particularly useful for non-invasive medical diagnosis, it may also be utilized for imaging the interior of materials other than living tissue. For example, the present specification may be used for geophysical imaging of the earth and oceans and other fields where it may be useful to image changes in the electrical conductivity of the object.

In certain embodiments, changes in electrical conductivity of an internal medium of a subject of interest (e.g., biological material) may be determined by performing measurements on an exterior surface of the subject of interest. In one embodiment, the measurements may be performed by disposing a plurality of electrodes on the exterior surface of the biological material. Further, some or all of the plurality of electrodes may be operatively coupled to the biological material.

For the purpose of electrical impedance imaging, determined current patterns may be applied to one or more electrodes of the plurality of electrodes at one or more instants in time and resultant voltages may be measured at the one or more electrodes. It may be noted that the measured or resultant voltages are representative of voltage drops along a current pathway which includes both the internal impedance and a boundary contact impedance. Further, as will be appreciated, safety levels for currents applied to human subjects are governed by regulations. The currents applied to the human subjects may include intended currents that are generated for a desirable use, unintended currents, currents generated due to a fault in the imaging system, or combinations thereof. In one example, the desirable amounts of currents in the current patterns comply with existing safety standards, such as, but not limited to, IEC 60601-1 standards.

Further, it may be noted that contact impedance exists at an interface between an electrode and a surface of the subject of interest, where the electrode is operatively coupled to the surface of the subject of interest. In one example, in case of the electrode-skin contact, the contact impedance exists at the electrode-skin interface and may be referred to as electrode-skin contact impedance. The contact impedances at the interface may arise due to electrochemical properties of the electrodes themselves or due to physical or physiological conditions at the interface of the electrodes and the skin.

Additionally, when determined current patterns are applied to the one or more electrodes contact impedances at the interface of the electrode and the subject of interest contribute a large amount to the resultant voltages. These contact impedances may be due to electrochemical properties of the electrodes themselves or due to physical conditions at the interface of the electrodes and the subject of interest.

In one example, the contact impedances may vary with time due to electrode drift or a change in one or more of a moisture, pH, and thickness of the skin with time. It may be noted that the contact impedances at the interface of the electrodes and the skin are relatively large and time-varying. In particular, when the electrodes are in contact with the biological materials containing an epithelial layer, electrochemical reactions contribute to a substantial variation in the measured electrode-skin contact impedance over time. The variations in the electrode-skin contact impedance over time influences current density distribution in the internal medium of the biological material. Accordingly, changes in the electrode-skin contact impedance may undesirably modify the measured voltages at the surface.

In certain embodiments, it is desirable to have a determined precision and sensitivity in impedance imaging. Further, it may be noted that resultant voltages at the electrodes are relied upon for imaging purposes. Also, the resultant voltages may change with the change in the contact impedances. Therefore, the quality of the images may be adversely affected by the change in the contact impedances of the electrodes.

In certain embodiments, the systems and methods provided herein are configured to estimate changes in contact impedances of one or more electrodes. In one example, the systems and methods may be used to partially or completely remove the effect of the changes in the contact impedances from the measured resultant voltages. Accordingly, in some embodiments, the changes in the contact impedances may be estimated and the undesirable effect of the change in the contact impedance in reconstructed images may be at least partly compensated by using the methods and systems of the present specification.

Further, in some embodiments methods and systems for electrical impedance imaging of a subject of interest may be provided. Moreover, in certain embodiments, the systems and methods of the present specification are configured to image a medium via electrical impedance imaging using determined current patterns. Additionally, resultant voltages that appear at the electrodes as a result of the applied determined current patterns may be used to determine electrical properties at a plurality of locations in the subject of interest. In one example, the electrodes may be disposed on a human body for the purpose of producing a visual representation or image of the electrical properties, or spectral impedance imaging of regions inside the body.

Moreover, the methods and systems of the present specification are configured to compensate for varying contact impedances of one or more electrodes of the plurality of electrodes, where the one or more electrodes are in contact with one or more biological materials including faunas and floras, such as, but not limited to, humans. In certain embodiments, the methods and systems may utilize a plurality of electrodes that are applied to the outer surface of a torso to be examined in a non-invasive manner. Further, current patterns are applied to one or more electrodes to obtain data needed to reconstruct an electrical impedance image. By way of example, resultant voltages that appear on the electrodes in response to the applied current patterns may be measured, and the data representative of the applied current patterns and resultant voltages may be processed to generate two-dimensional (2D) or three-dimensional (3D) images of the interior conductivity and/or permittivity of the object or subject. In one example, reconstructive algorithms may be used to generate the 2D or 3D images.

In certain embodiments, undesirable changes in the contact impedances at the electrode-skin interface may be determined. In some embodiments, the changes in the contact impedances may be determined for a given period of time. Alternatively or additionally, in some other embodiments, the change in contact impedances may be determined for one or more pairs of electrodes.

Additionally, portions of the resultant voltages that are contributed by the change in the contact impedances may be determined. These portions of the resultant voltages contributed by the change in the contact impedances may be deducted from the resultant voltages to determine the compensated voltages at the electrodes. Accordingly, the compensated voltages represent the voltages that would have appeared at the electrodes had there been no undesirable change in the contact impedances. In some embodiments, the compensated voltages may be then used to reconstruct an image. Advantageously, images reconstructed using the compensated voltages are relatively more accurate representations of physiological features and parameters of the subject of interest as compared to images reconstructed without using the compensated voltages.

Figure 1:
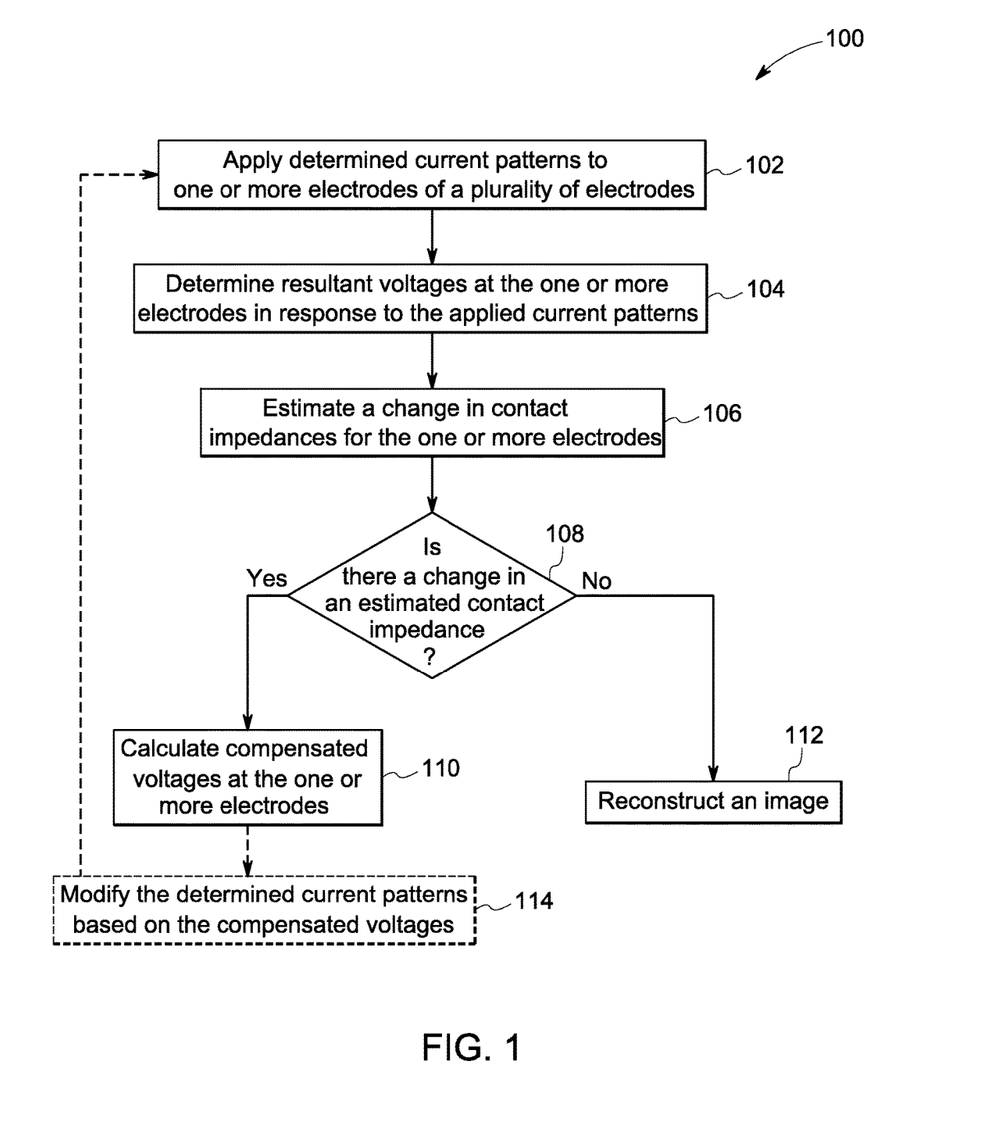
FIG. 1 is a block diagram of an example method for impedance imaging of a subject of interest using a plurality of electrodes, in accordance with aspects of the present specification.

FIG. 1 illustrates a flow diagram 100 of an example method for electrical impedance imaging of a subject of interest using a plurality of electrodes. The method provides provisions for compensating for a change in contact impedances of one or more electrodes of the plurality of electrodes. Further, in some embodiments, the images may be compensated to account for the change in the contact impedances. In certain embodiments, the images may be reconstructed in real-time during imaging. Whereas, in certain other embodiments, the images may be modified at a later point in time to compensate for the change in the contact impedances.

In certain embodiments, the method may be iterative in nature. In these embodiments, the estimated change in the contact impedances may be used to modify the determined current patterns for one or more electrodes. The modified current patterns may be then applied to the one or more electrodes, and the change in the contact impedances may be measured accordingly.

At block 102, determined current patterns may be applied to one or more electrodes of the plurality of electrodes. In an alternative embodiment, the determined current patterns may be applied as pairwise current patterns. In this embodiment, determined current patterns may be applied for each pair of electrodes of the plurality of electrodes.

In one embodiment, the determined current patterns may be configured to maximize the ability of the plurality of electrodes to detect changes in an internal medium given a constrained input power, where the constrained input power may be defined by safety concerns. Further, in some embodiments, the determined current patterns may be optimal current patterns that are configured to maximize percent distinguishability. As used herein, the term "percent distinguishability" is represented by Eq. (1)

$$D = 100 \max_k \frac{\sum_{j=1}^{N} |I_{j,k} V_{j,k}(t_T) - I_{j,k} V_{j,k}(t_o)|}{\sum_{j=1}^{N} |I_{j,k} V_{j,k}(t_o)|} \quad (1)$$

where $I_{j,k}$ is the current applied on an electrode j for a given current pattern k, N is the number of electrodes, and $V_{j,k}$ is the voltage measured on the electrode j for the given current pattern, t is a temporal variable representative of time. The time at the beginning of imaging may be represented as t=0. Similarly, the time at a determined period of time after the imaging has started may be represented as t=T.

Further, it may be noted that distinguishability may vary with respect to time due to physiological changes and/or the electrode drift. Moreover, when distinguishability due to the electrode drift is relatively large, physiological changes that possess a lower distinguishability are not observable. Thus, it is desirable to compensate for the electrode drift to reduce the distinguishability such that the system remains suitably sensitive to observe the desirable physiological changes.

At block 104, resultant voltages in response to the applied determined current patterns may be determined for the one or more electrodes. Further, in certain embodiments, the resultant voltages may be determined for each individual electrode of the one or more electrodes. By way of example, a determined current pattern may be applied to an electrode and a resultant voltage may be determined for the same electrode. Whereas, in certain other embodiments, pairwise current patterns may be applied. In these embodiments, the resultant voltages may be determined for one or more pairs of the electrodes. Additionally, in embodiments where optimal current patterns are applied to the plurality of electrodes, the resultant voltages for each individual electrode or the one or more pairs of electrodes may be determined using mathematical decomposition.

Further, in some embodiments, the resultant voltages may be determined at two or more instants in time. In one example, the resultant voltages may be determined for a given electrode at the beginning of imaging (t=0) and at a determined period of time (t=T). Additionally, in some embodiments, the resultant voltages may be determined for the pairs of electrodes at two or more instants in time.

At block 106, a change in contact impedances may be estimated for the one or more electrodes of the plurality of electrodes. In some embodiments, the change in the contact impedances may be estimated for each pair of electrodes of the plurality of electrodes. Alternatively, in some other embodiments, the change in the contact impedances may be estimated for each electrode of the one or more electrodes for two or more instants in time. In one embodiment, the change in the contact impedances may be estimated for each pair of electrodes of the one or more electrodes for two or more instants in time.

Estimating the change in the contact impedances may include estimating individual contact impedances for a given electrode at two or more instants in time, and determining the difference between the contact impedances at the two or more instants in time. Alternatively, estimating the change in the contact impedances may include estimating individual contact impedances of a pair of electrodes, and determining the change in the contact impedance for the pair of electrodes based on the estimated individual contact impedances. Further, in some embodiments, the contact impedances may be estimated using predefined fitting models. For example, the contact impedances may be estimated using a least-square fit model.

In certain embodiments, the contact impedances may have complex values that have real and imaginary parts. In some embodiments, the contact impedances may be estimated using a resistance based model. Further, in the case of the resistance model, it may be assumed that the contact impedances may have real and positive parts. Alternatively, in some other embodiments, a series resistance-capacitor model may be used to estimate the complex impedances. Further, in the case of the resistance-capacitance model, it may be assumed that the values of the contact impedances may be represented as complex values that have a positive real part and a negative imaginary part. Moreover, in certain embodiments, the contact impedances may be estimated using a parallel resistance-capacitor model. Additionally, in these embodiments, the real part may be constrained to be positive and the imaginary part may be constraint to be negative.

Additionally, depending on the predefined model that is selected to estimate the contact impedances further constraints may be provided based on one or more predefined constraints. By way of example, minimum and maximum values of resistance and capacitance may be assumed when using the series or parallel resistance-capacitor models.

Although discussed with respect to resistances, the change in contact impedances may be estimated using a change in one or more properties over time. Non-limiting examples of such properties may include electrical conductivity, permittivity, and frequencies of currents of the current patterns with respect to time.

In certain embodiments, the estimated contact impedances may be filtered. In one embodiment, the estimated contact impedances may be filtered to exclude desired signal changes in the impedances of the internal medium. In one example, in these embodiments, the estimated contact impedances may be filtered to remove changes in the contact impedance that are contributed by physiological phenomenon. For example, the changes in the contact impedances due to physiological phenomenon, such as, but not limited to, heart or breathing signals may be filtered out from the estimated contact impedances. Further, in another example, filtering may be performed to remove expected temporal or spectral physiological signals from the estimated changes in the contact impedances. Moreover, in one example, filtering may be performed to exclude physiological signals by fitting the estimated change in the contact impedances to an exponential function based on electrode drift time constants.

Additionally or alternatively, in another embodiment, the estimated contact impedances may be filtered to retain desired changes in the contact impedances due to the electrode-skin interface. By way of example, the estimated contact impedances may be filtered to retain contribution in the change of the contact impedance due to drift in the electrode. Further, in one example, filtering may be performed to include expected changes in temporal or spectral contact impedances while estimating the changes in the contact impedances. In some embodiments, filtering may include fitting contact impedance change vs. time to a desirable model. Non-limiting examples of the desirable model may include an exponential function, a linear function, a quadratic function, a $3^{rd}$ order function, a function having an order higher than the $3^{rd}$ order, or combinations thereof.

In some embodiments, a plurality of current frequencies may be used in the determined current patterns to verify or to provide additional data to further enhance the estimation of the change in the contact impedances. Moreover, in estimating the change in the contact impedance it may be assumed that the internal medium of the subject of interest remains constant.

At block 108, it may be determined whether there has been a change in the contact impedance for each electrode or each pair of electrodes of the one or more electrodes. By way of example, if the estimated value of the change in the contact impedance (block 106) for an electrode is zero, it signifies that there has been no change in the contact impedance. Further, if the estimated value of the change in the contact impedance for a given electrode is a non-zero value, it suggests that the contact impedance for that particular electrode or pair of electrodes may have changed.

At block 110, if there is a change in the contact impedances of the one or more electrodes of the plurality of electrodes, compensated voltages for each individual electrode or each pair of electrodes may be calculated based on the estimated change in the contact impedances. In some embodiments, the compensated voltages may be calculated by subtracting a portion of the voltage from the resultant voltage, where the portion of the voltage corresponds to the change in the contact impedance.

In instances where there is no change in the contact impedance of any of the electrodes or the pair of electrodes, the reconstruction of the image may be performed without modifying the values of the resultant voltages to compensate for the change in the contact impedances. Accordingly, as indicated by block 112, images may be reconstructed based on the determined current patterns, the resultant voltages, and the compensated voltages.

Optionally, at block 114, in one embodiment, the determined current patterns may be modified based on the estimated changes in the contact impedances. The modified current patterns may then be applied, and corresponding resultant voltages, changes in the contact impedances, and compensated voltages may be measured for the modified current patterns. In this manner, the method for compensating for the change in the contact impedances may be performed in an iterative fashion. Accordingly, in certain embodiments, after determining the modified current patterns, steps represented in blocks 102 to 112, and optionally step 114 may be repeated one or more number of times. Moreover, the number of iterations may be decided by a user operating the imaging system. Alternatively, the number of iterations may be decided based on one or more parameters, such as, but not limited to, a difference in values of the resultant voltages and the compensated voltages, or distinguishability criteria in the reconstructive images.

Figure 2:
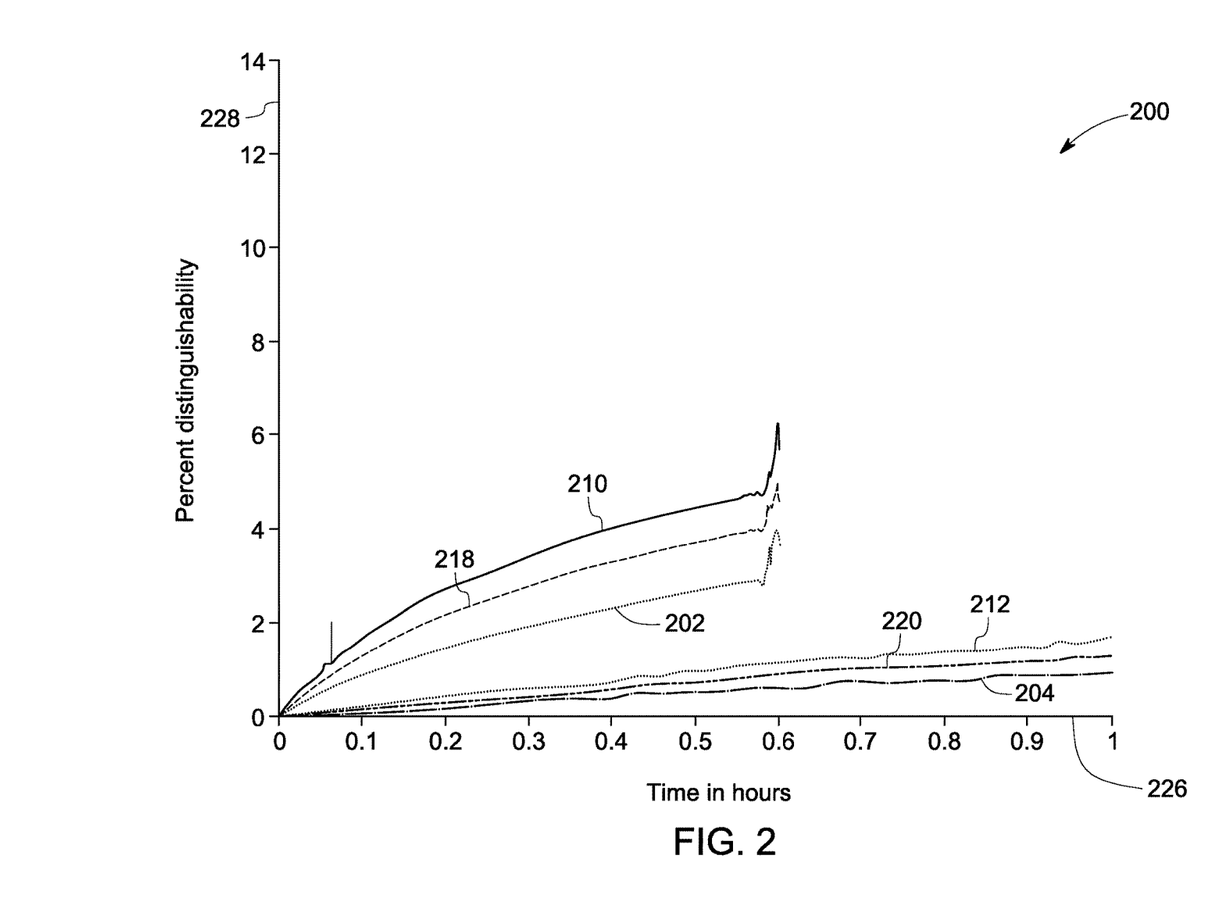
FIG. 2 is a graphical representation of a distinguishability metric before compensation for a change in contact impedances for different objects and subjects as well as a change in impedance of an internal medium of one of the subjects over a time period of 1 hour, in accordance with aspects of the present specification.

FIG. 2 illustrates a graphical representation 200 of a change in a distinguishability metric for different objects and/or subjects as well as that of internal medium of one of the subjects over a time period of 1 hour. In the illustrated embodiment, a change in contact impedances changes the values of maximum, minimum and total distinguishability. Accordingly, with the change in the contact impedances the value of the total distinguishability factor for these subjects is altered. Curves 202 and 204 represent changes in the minimum distinguishability of the different subjects, while curves 210 and 212 represent changes in the maximum distinguishability of the subjects. Curves 218 and 220 represent changes in the total distinguishability of the subjects. Abscissa 226 represents time in hours, ordinate 228 represents the percent distinguishability.

Figure 3:
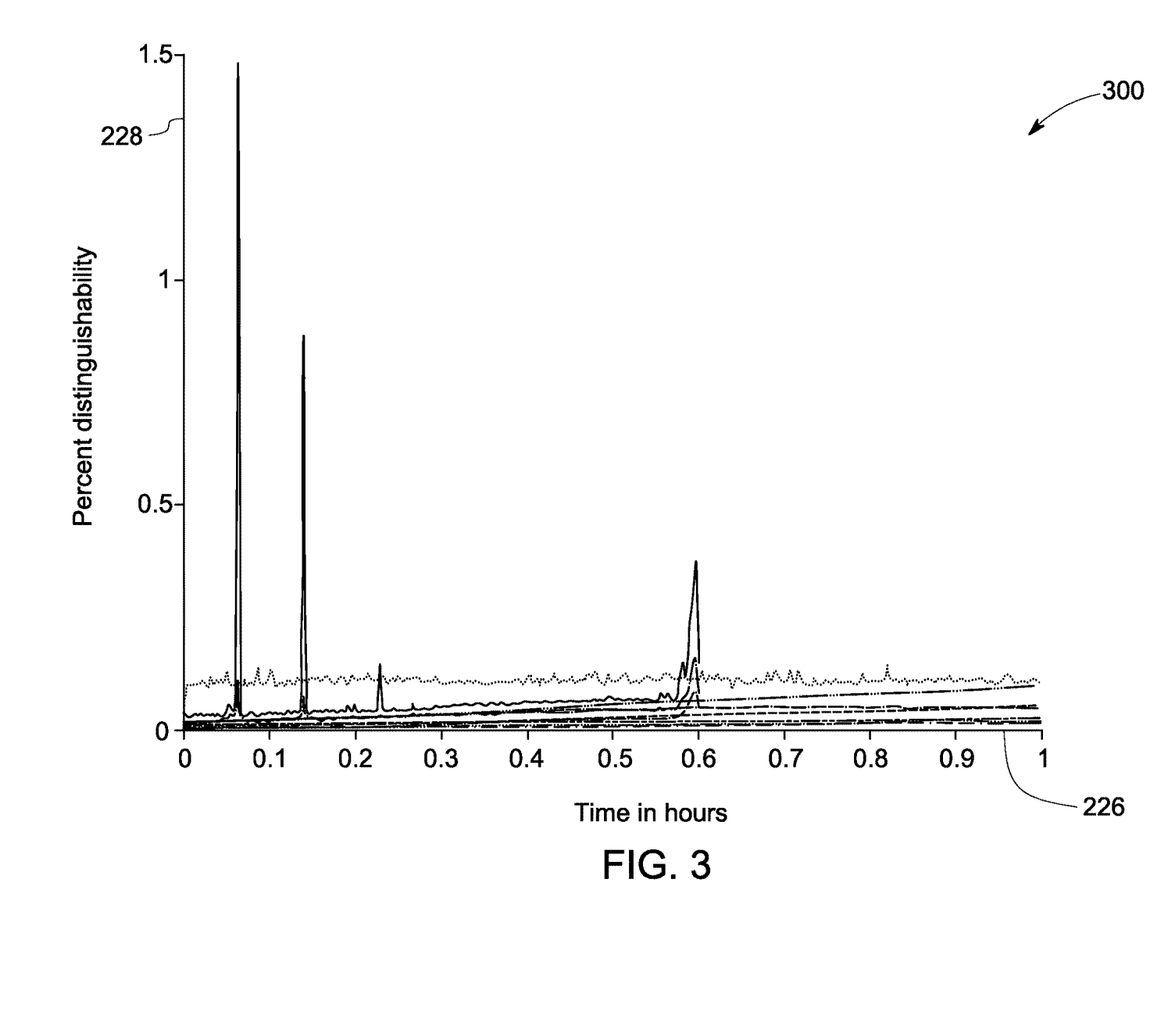
FIG. 3 is a graphical representation of the distinguishability metric after compensation for a change in contact impedances, in accordance with aspects of the present specification.

FIG. 3 illustrates a graphical representation 300 of distinguishability after compensation for the changes in the contact impedances of FIG. 2. As illustrated, the maximum, minimum and total distinguishability are reduced and have relatively lower amount of change over time after the compensation of the changes in the contact impedances.

Figure 4:
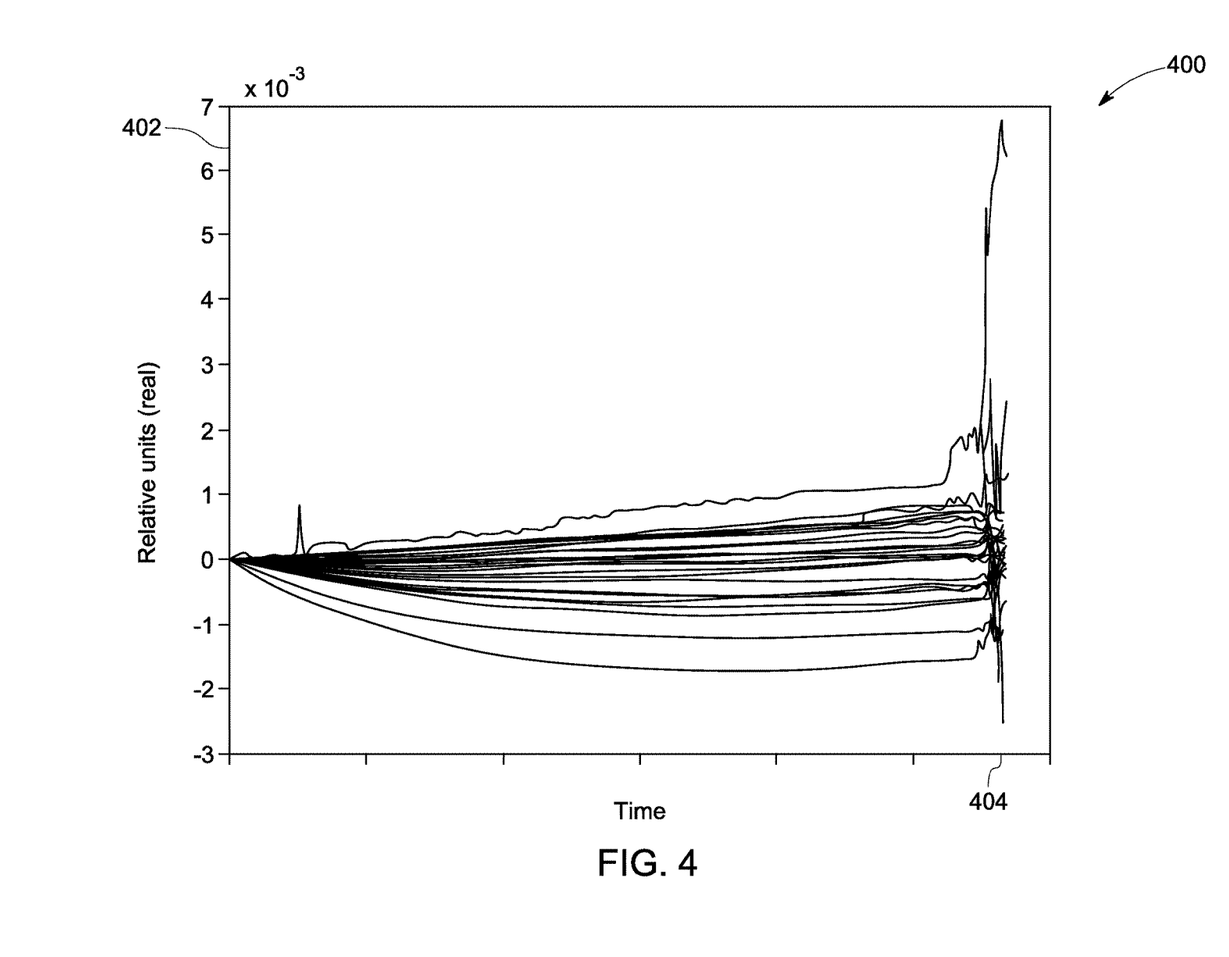
FIG. 4 is a graphical representation of real values of estimated changes in the contact impedances for 32 electrodes over a period of time, in accordance with aspects of the present specification.
Figure 5:
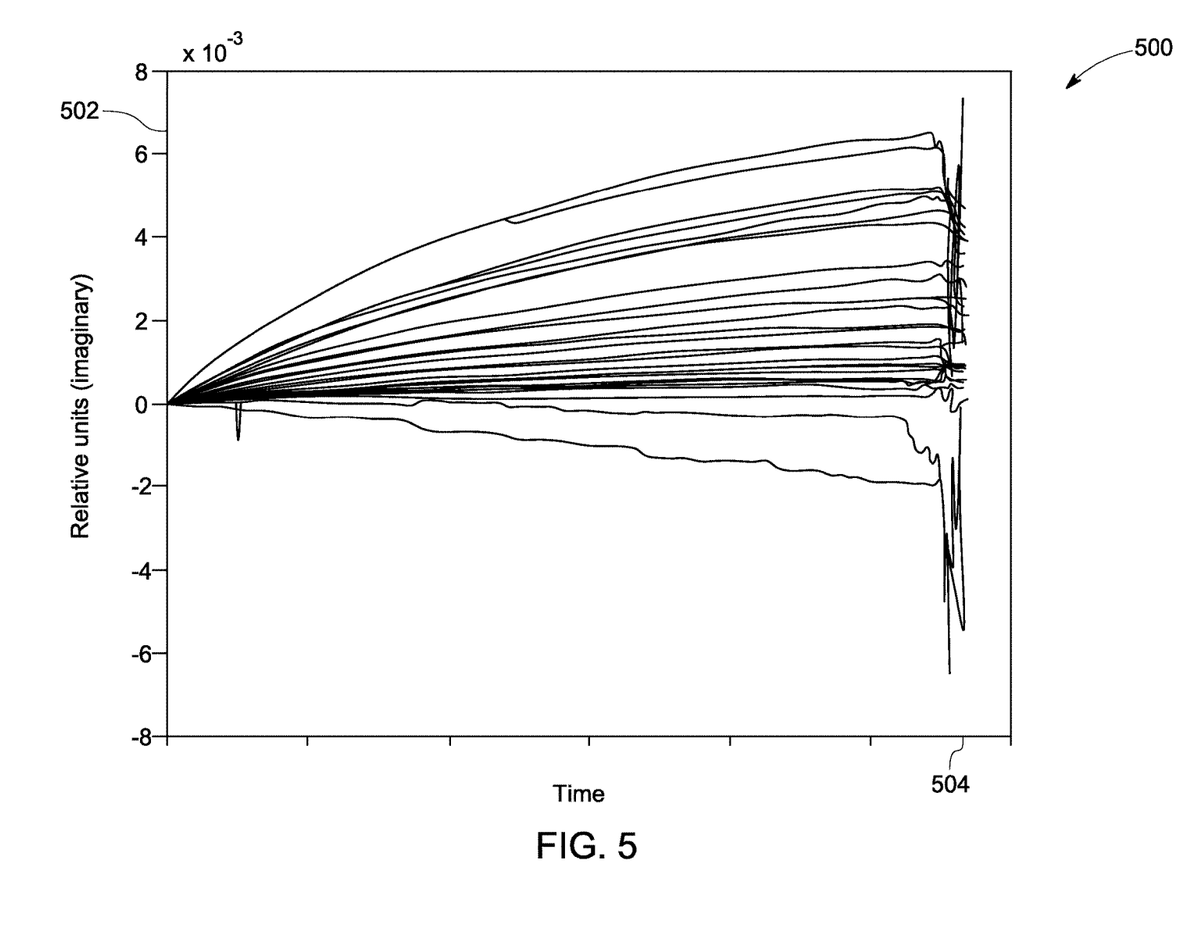
FIG. 5 is a graphical representation of imaginary values of estimated changes in the contact impedances for 32 electrodes over a period of time, in accordance with aspects of the present specification.

FIG. 4 illustrates a graphical representation 400 of real values (axis 402) of the estimated changes in the contact impedances over a period of time (axis 404) for a plurality of electrodes having 32 electrodes. FIG. 5 illustrates a graphical representation 500 of imaginary values (axis 502) of estimated changes in the contact impedances for 32 electrodes over time (axis 504). In the illustrated embodiment, the change in the contact impedances may be determined assuming that there is global change in internal impedance, and that there are no local changes in the internal impedance of the subject.

Figure 6:
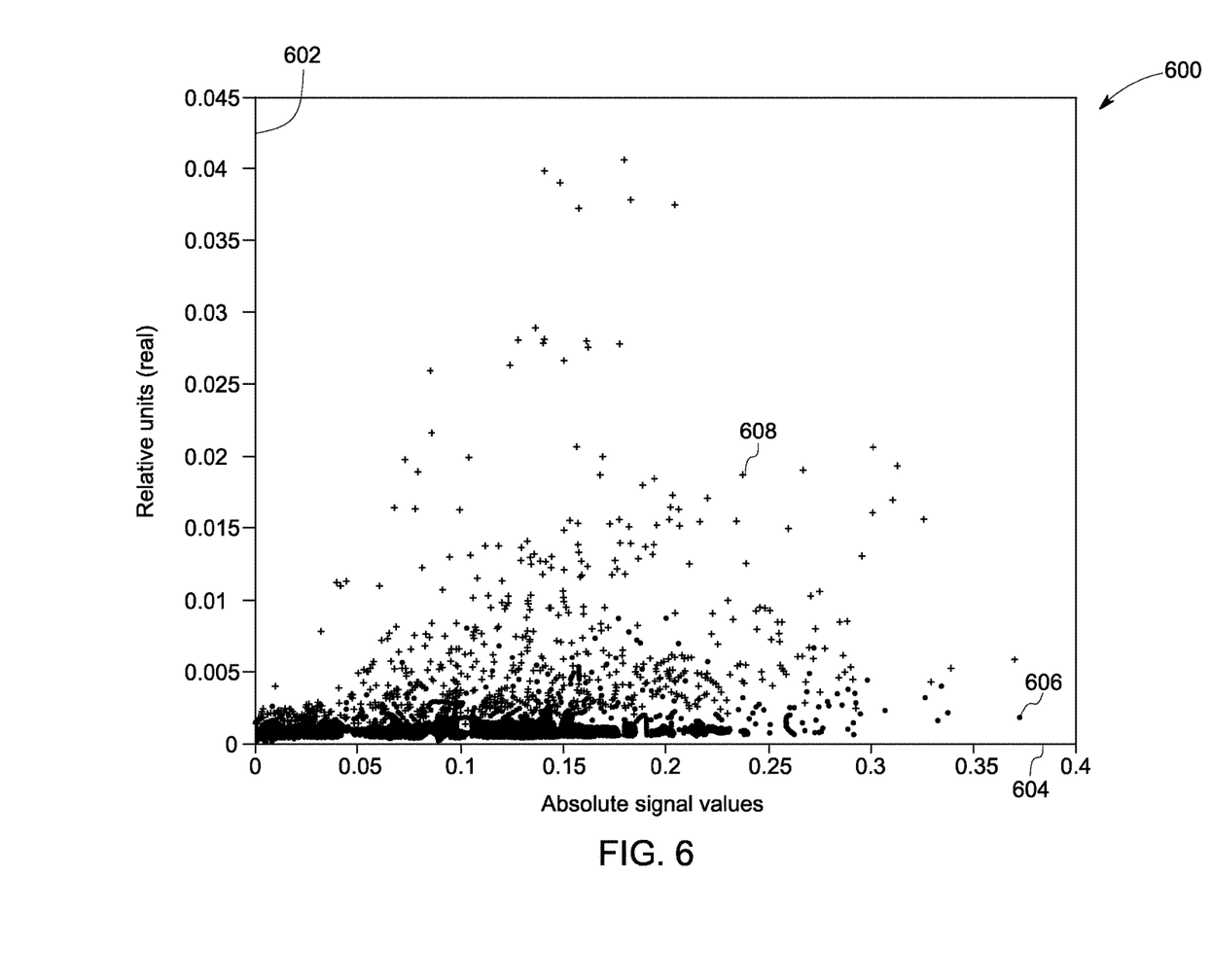
FIG. 6 is a graphical representation of compensated and uncompensated changes in real values of complex contact impedances over a period of about 45 minutes, in accordance with aspects of the present specification.
Figure 7:
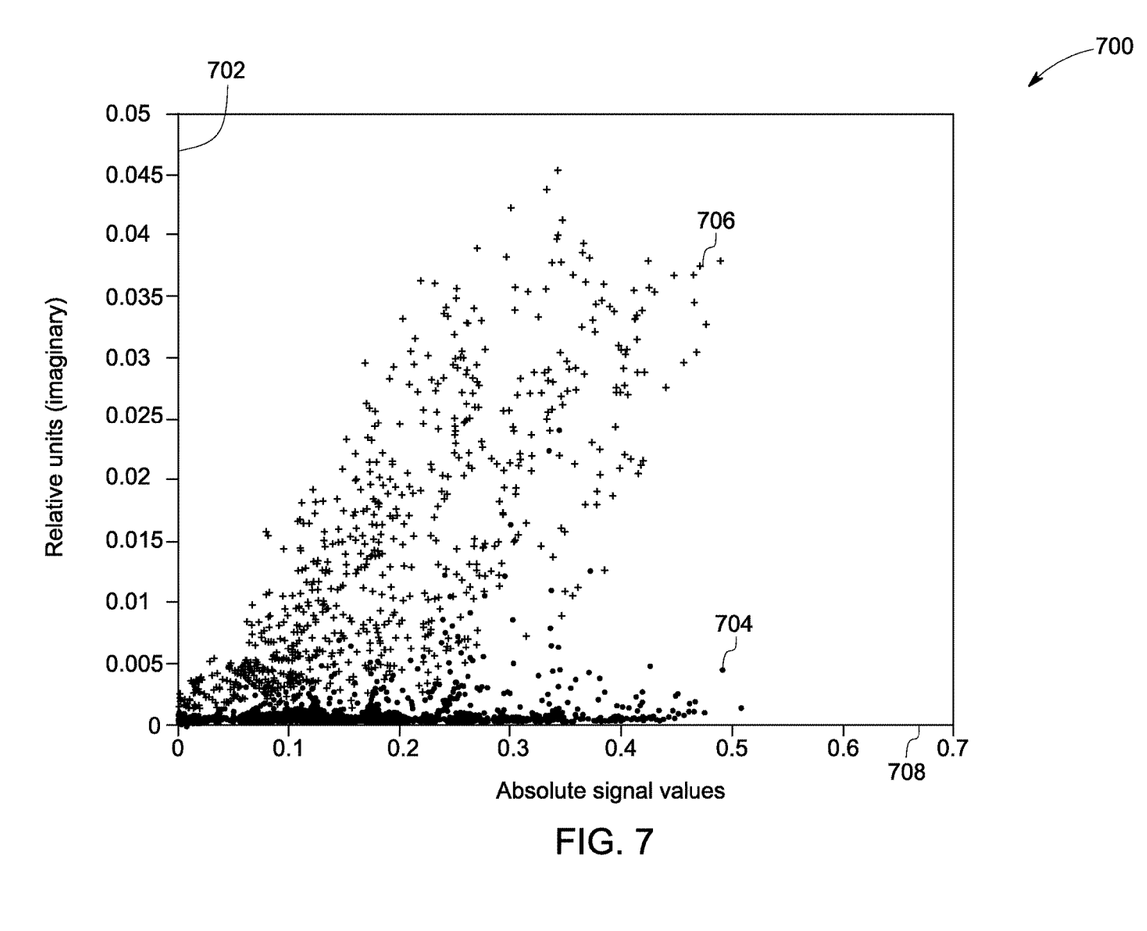
FIG. 7 is a graphical representation of compensated and uncompensated changes in imaginary values of the complex contact impedances over a period of about 45 minutes, in accordance with aspects of the present specification.

FIG. 6 illustrates a graphical representation 600 of a comparison between compensated changes 606 and uncompensated changes 608 of the complex contact impedance over a period of time (axis 604). As illustrated, the real values of the compensated contact impedances 606 exhibit lower amount of variation (axis 602) as compared to the real values of the uncompensated contact impedances. Similar to FIG. 6, FIG. 7 illustrates a graphical representation 700 of compensated changes 704 and uncompensated changes 706 in imaginary part of the contact impedance measurements over a period of time (axis 708). As illustrated, the imaginary values of the compensated contact impedances 606 exhibit lower amount of variation (axis 702) as compared to the imaginary values of the uncompensated contact impedances.

Figure 8:
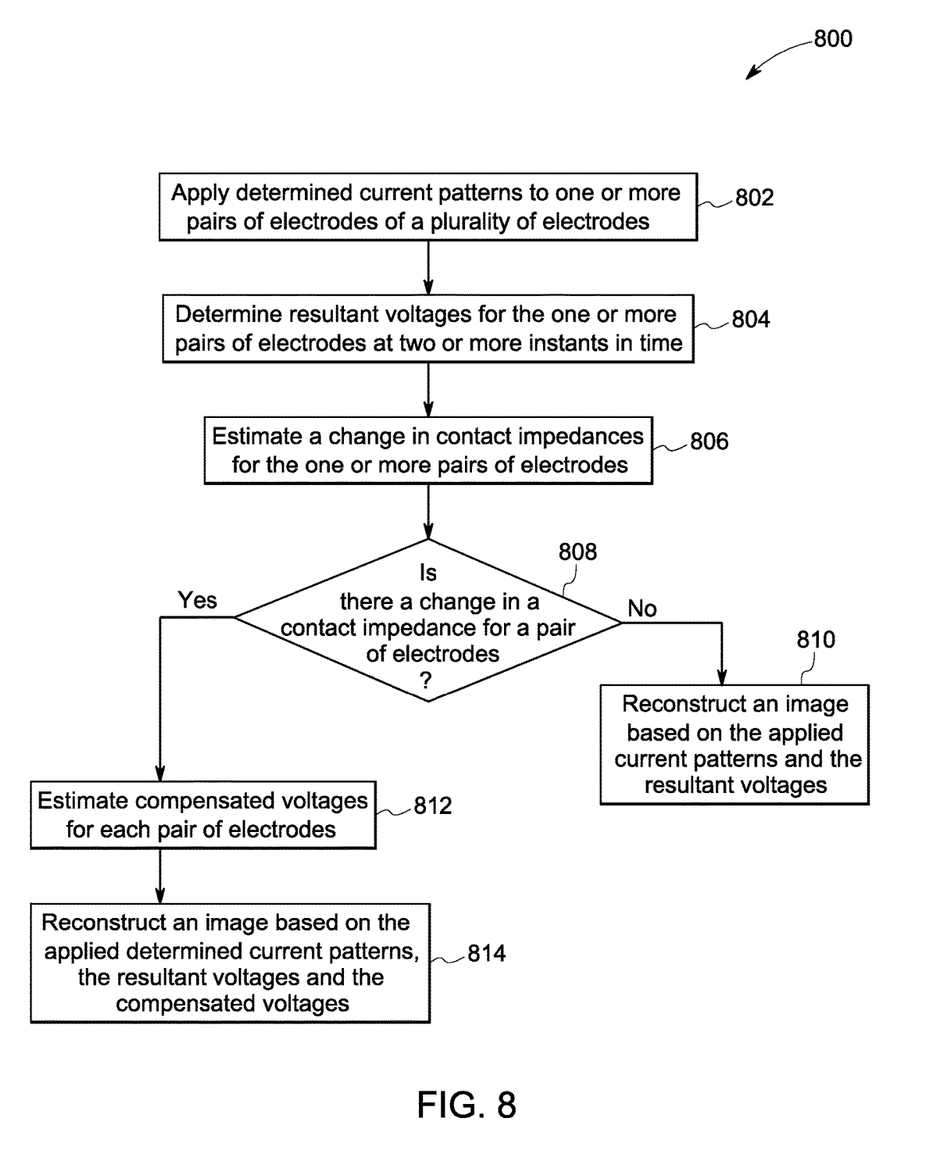
FIG. 8 is a block diagram of an example method for impedance imaging of a subject of interest using pairwise measurements, in accordance with aspects of the present specification.

FIG. 8 illustrates a flow diagram 800 of an example method for imaging a subject of interest using electrical impedance imaging. The method includes compensating at least in part for a change in contact impedances of one or more electrodes of a plurality of electrodes.

At block 802, the method commences by applying determined current patterns to one or more pairs of electrodes of the plurality of electrodes. Further, at block 804, corresponding resultant voltages may be measured for the one or more pairs of electrodes. The resultant voltages may be measured at two or more instants in time at the one or more pairs of electrodes. In one example, the resultant voltages may be measured at the beginning of imaging, represented by t=0. Further, the resultant voltages may be measured at another instant in time, represented by t=T.

At block 806, a change in the contact impedances may be estimated for one or more pairs of the electrodes. In one embodiment, a resistance based model may be used to estimate the change in the contact impedances for each pair of electrodes. In this embodiment, resistances may be computed for each pair of electrodes at t=0 and t=T instants in time. It may be noted that t=T may represent any time during or immediately after imaging.

In some embodiments, the change in a contact impedance for each electrode may be approximated as a single complex impedance generally represented as $r\{i\}(t)$. Thus, for a given set of determined current patterns and resultant voltages and assuming the linearity of the system, the resultant voltages due to the current patterns in which only two electrodes carry current may be synthesized using mathematical decomposition. In one example, contact impedances between electrodes i and j, generally represented as $R\{i,j\}(t)$ may be determined from the resultant voltages that may be produced by application of a current of +1 Amps on an electrode represented as i and −1 Amps on an electrode represented as j. It should be noted that application of currents having values of +1 Amp and −1 Amp on the electrodes is merely for example purposes. In practice currents having values equal to or greater than about +1 Amp and −1 Amp may not be considered suitable for biological materials.

Further, a matrix, $R\{i,j\}(0)$, representative of the resistances at t=0 may be formed using the individual resistances, $r\{i\}(0)$, at t=0. Moreover, a matrix, $R\{i,j\}(T)$, may be formed from the individual resistances $r\{i\}(t)$, at t=T. Pairwise resultant voltages may be measured, and a matrix of resistances, $R\{i,j\}(t)$ may be computed, where i and j are electrodes. In one embodiment, $R\{i,j\}(t)$ may have a dimension N×N, where N is the number of electrodes. Further, it may be noted that a constant may be added to the compensated voltages so the sum of the compensated voltages is zero.

In some embodiments, the change in contact impedances may be estimated as a function of time. In a non-limiting example, the change in contact impedances may be estimated using a least-square fit algorithm. In one embodiment, a least-square fitting approach may be used to model the change in $R\{i,j\}(T)$ as series resistance changes 40 and $r\{j\}$, in addition to a global shift in the impedance.

In certain embodiments, the resistance of the internal medium of the subject of interest between the i-th and j-th electrodes at an instant t in time may be represented as a difference between the resultant voltages. In one embodiment, the resistance of the internal medium between the i-th and j-th electrodes at time t may be represented by Eq. (2). Eq. (2) may be repeated for each pair of electrodes.

$$R\{i,j\}(t)=r\{i\}(t)+R_{medium}\{i,j\}+r\{j\}(t) \qquad (2)$$

A resistance matrix for all pairs of electrodes at a given time may be represented as $R\{i,j\}(t)$ as represented by Eq. (2). In one embodiment, a least-squares fitting procedure may be used to estimate the changes in $r\{i\}$ and $r\{j\}$ for electrodes i and j that account for a maximum change in the resistance matrices between two time points, t1 and t2. It may be assumed that the internal medium itself is not time-varying.

Additionally, a model may be provided to estimate a change in the resistances of each pair of electrodes to estimate a change in the contact impedances between each pair of electrodes. Eq. (3) represents an example model for estimating a change in the resistances.

$$R\{i,j\}(t)-R\{i,j\}(0)=\delta r\{i\}(t)+\delta r\{j\}(t)+c(t)R\{i,j\}(0) \qquad (3)$$

Using the model represented by Eq. (3) resistances $\delta r\{i\}(t)$, $\delta r\{j\}(t)$, and constant $c(t)$ may be determined for various points in time, and for each pair of electrodes.

At block 808, an assessment may be made as to whether there is a change in the contact impedance between a given pair of electrodes. If there is no change in contact impedance for the one or more pairs of electrodes, at block 810, an image may be reconstructed based on the applied current patterns and resultant voltages.

However, if there is a change in the contact impedances for the one or more pairs of electrodes, at block 812, compensated voltages may be estimated for each of the one or more pairs of electrodes. In some embodiments, for each pair of electrodes, estimated changes in the contact impedances may be used to modify the resultant voltages corresponding to the electrodes to account for a drop in voltage at each of the electrodes due to inadvertent change in the contact impedance of each of the electrodes as represented in Eq. (4).

$$V_{compensated}\{j\}(t)=V_{uncompensated}\{j\}(t)-(\delta r\{j\}(t))I\{j\}(t) \qquad (4)$$

where $V_{compensated}$ is the compensated voltage, $V_{uncompensated}$ is the measured voltage and I is the applied determined current pattern.

At block 814, an image may be reconstructed based on the values of the applied determined current patterns, the resultant voltages, and the compensated voltages. Optionally, after block 812, the compensated voltages may be used to modify the current patterns, and the modified current patterns may be applied to each of the one or more pair of electrodes. Further, steps 804-814 may be repeated one or more number of times depending on a desirable sensitivity in the reconstructed image.

In some embodiments, the estimated change in the contact impedances may be used to adjust voltages for the one or more pairs of electrodes to remove a voltage drop from the electrodes. Further, it may be noted that in the embodiments of FIGS. 1 and 8, the image may be reconstructed simultaneously while compensating for the change in the contact impedance. In this embodiment, the reconstructed image may be corrected based on the compensated change in the contact impedance. Alternatively, an image may be reconstructed, and subsequently, the image may be modified to remove the effect of the change in the contact impedance from the reconstructed image.

Further, in the embodiments of FIGS. 1 and 8, the determined current patterns facilitate identification of inhomogeneities in electrical impedance imaging. In certain embodiments, the determined current patterns may be obtained by optimizing the distinguishability. The optimal distinguishability may be selected such that the presence of a conductivity perturbation inside a volume conductor changes the current density distribution. If this change in the current density distribution yields a detectable change in measured surface potentials, then the perturbation may be considered distinguishable.

Moreover, in certain embodiments, the pairwise current patterns may include complete and orthogonal sets of current patterns. Also, it is assumed that the current applied to each electrode is the intended applied current.

In embodiments where the contact impedances may be determined for individual electrodes using determined current patterns that are applied to the individual electrodes. In these embodiments, single resultant voltages may be measured for each single current pattern. Further, pairwise impedances may be synthesized based on assumed currents and the measured single voltage differences alternately using the measured currents.

The methods 100 and 800 are described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as a memory, and in operative association with a processor unit. In certain other embodiments, the computer executable instructions may be located in computer storage media, such as memory storage devices, that are removed from the imaging system. Moreover, the method for compensating for the change in contact impedance may include a sequence of operations that may be implemented in hardware, software, or combinations thereof.

Figure 9:
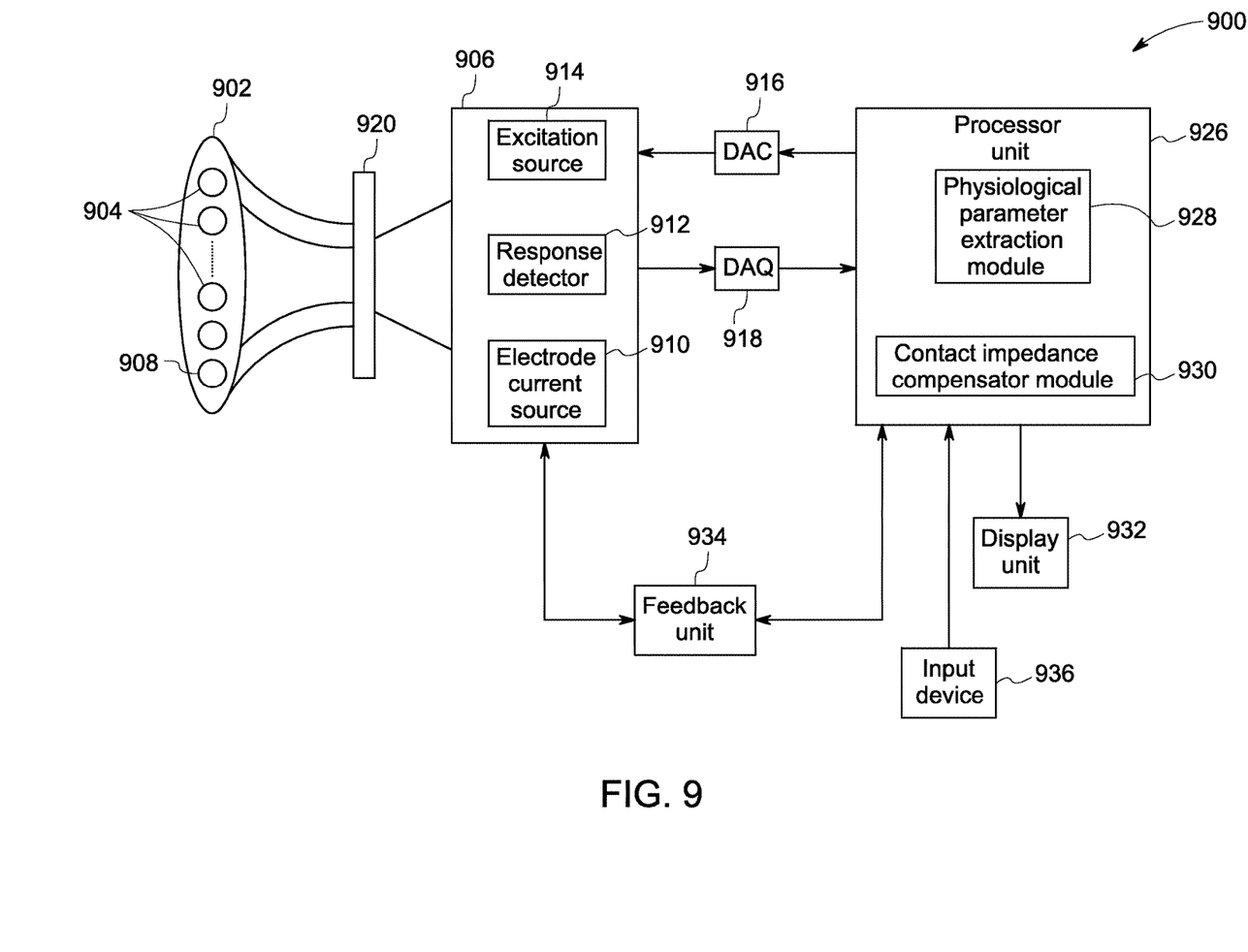
FIG. 9 is a schematic representation of an electrical impedance imaging system having a contact impedance compensator module, in accordance with aspects of the present specification.

FIG. 9 illustrates an example electrical impedance imaging system 900 in accordance with aspects of the present specification. In the illustrated embodiment, the electrical impedance imaging system 900 may be used to obtain electrical impedance measurements of an object 902 (e.g., a patient or subject). The electrical impedance imaging system 900 is an electrode based system. Further, in the illustrated embodiment, the electrical impedance imaging system 900 includes a plurality of electrodes 904 disposed at or proximate a surface of the object 902. By way of example, in a healthcare application (e.g., patient monitoring) the plurality of electrodes 904 may be attached to the skin of a patient using a suitable adhesive. The electrodes 904 of the plurality of electrodes 904 may be positioned on the surface of the object 902 in different arrangements and may be driven in different configurations. For example, in one embodiment, the electrodes 904 may be positioned to provide different views of trajectories or angles. In one example, electrodes 904 may be positioned to provide different views of trajectories or angles through the lungs, the torso, or both. Moreover, in one example, the views of different trajectories or angles may be used to provide increased sensitivity to breathing and decreased sensitivity to ambulatory motion.

In certain embodiments, the electrodes 904 may be formed from any suitable conductive material used to establish a desirable excitation. For example, the electrodes 904 may be formed from one or more metals such as copper, gold, platinum, steel, silver, and alloys thereof. Other suitable materials for the electrodes 904 may include non-metals that are electrically conductive, such as a silicon based materials used in combination with micro-circuits. In one embodiment, where the object 902 is a human body region, the electrodes 904 may be formed from silver-silver chloride. Additionally, the electrodes 904 may be formed in different shapes and/or sizes, for example, as rod-shaped, flat plate-shaped or needle-shaped structures.

In operation, the electrodes 904 may be used to deliver an electrical current to the object 902 in a continuous or modulated manner such that excitations may be applied across a temporal frequency range (e.g., 100 Hz to 1 MHz) to the surface of the object 902 to generate an electromagnetic field within the object 902. The resulting voltages (real, imaginary or complex) on the electrodes 904 may be measured to determine an electrical impedance (e.g. electrical conductivity or permittivity distribution), which is used to separate or distinguish different physiological parameters.

As noted hereinabove, contact impedances may exist at an interface between an electrode and a material that the electrode is physically in contact with. In one example, in case of the electrode skin contact, the contact impedance exists at the electrode-skin interface and may be referred to as electrode-skin contact impedance.

Further, in some embodiments, currents driving one or more electrodes 904 may be at different frequencies. In other embodiments, the currents driving the one or more electrodes 904 may be at the same or substantially similar frequencies. In some of these embodiments, the currents having the same or substantially similar frequency may have different phases (e.g., 0 degrees, 90 degrees, 180 degrees and 270 degrees). It should be noted that some of the electrodes 904 may have no current applied thereto. Such electrodes 904 may be used only for voltage measurements.

Moreover, the plurality of electrodes 904 may include a reference electrode 908. The reference electrode 908 is configured to receive currents from all the electrodes 904. Accordingly, a reference current at the reference electrode 908 is a cumulative sum of the currents applied to the various electrodes 904. Also, the reference electrode 908 is attached to the object to provide a reference potential and may not be intended to source or sink the current during normal operation. In one example, the plurality of electrodes 904 may have 32 electrodes to which currents are applied. Although not illustrated, in some embodiments, two or more reference electrodes 908 may be employed in the electrical impedance imaging system 900.

Additionally, in certain embodiments, the electrodes 904 may be operatively coupled to a plurality of electrical channels 906. Although the illustrated embodiment shows only one electrical channel 906, it may be noted that the electrical impedance imaging system 900 may employ a plurality of electrical channels 906. Each electrical channel 906 may include an electrode current source 910, an excitation source 914 and a response detector 912.

Further, in one embodiment, each electrode 904 of the plurality of electrodes 904 may be operatively coupled to a corresponding electrical channel 906 of the plurality of electrical channels 906. Each electrical channel 906 of the plurality of electrical channels 906 may be configured to provide a desirable amount of current to the corresponding electrode 904 of the plurality of electrodes 904. Further, the desirable amount of current may be below a threshold value of the applied current. Further, the electrical channels 906 may be configured to be de-energized or operatively disconnected from the plurality of electrodes 904. In one example, the plurality of channels 906 may be disconnected from their respective electrodes 904 using an electrically controlled switch (e.g., an output relay) configured to de-energize the corresponding channel 906 when an output current to the subject is higher than the safe threshold value.

Also, in addition to the electrode current source 910, each electrical channel 906 may include an excitation driver or excitation source 914 and a response detector 912 that are coupled to the electrodes 904. Also, the excitation source 914 and the response detector 912 are each connected to a processor unit 926 (e.g., a computing device). In one embodiment, the excitation source 914 and the response detector 912 are physically separate devices. In other embodiments, excitation source 914 and the response detector 912 are physically integrated as one element. The processor unit 926 may transmit instructions to the excitation source 914 through a digital to analog converter (DAC) element 916 and receives data from the response detector 912 through a data-acquisition (DAQ) element 918. It should be noted that one or more excitation sources 914 may be provided such that one excitation source 914 is provided per electrode 904, for a subset of electrodes 904 or for all the plurality of electrodes 904.

In various embodiments, a multi-wire measurement configuration is provided that uses different electrodes 904 for excitation from the excitation source 914 and measurement by the response detector 912. Further, in one embodiment, two or more electrical channels 906 may share the same excitation source 914 and/or the response detector 912. The electrical channels 906 may be operatively coupled to their respective electrodes 904 using an interface 920. In particular, the connection between the electrodes 904 and one or both of the excitation source 914 and the response detector 912 may be provided via the interface 920. In various embodiments, the excitation source 914 applies an excitation current to one or more of the electrodes 904 with a voltage response measured by one or more electrodes 904.

Further, a physiological parameter extraction module 928 may be implemented within the processor unit 926. Further, the physiological parameter extraction module 928 may be implemented within the hardware or a combination of the software and hardware. In addition to the physiological parameter extraction module 928, the processor unit 926 may also include a contact impedance compensator module 930. In certain embodiments, the contact impedance compensator module 930 is configured to provide compensation at least in part for a change in the contact impedance of one or more electrodes 904. The contact impedance compensator module 930 may include software and/or hardware that are configured to execute determined process steps to compensate for the change in contact impedances. Further, the contact impedance compensator module 930 may include computer executable instructions in the form of routines, programs, objects, components, data structures, procedures, modules, functions, and the like that perform determined process steps. Moreover, the contact impedance compensator module 930 may include a sequence of operations that may be implemented in hardware, software, or combinations thereof.

Additionally, the system 900 may further include a display unit 932 configured to display the data processed by the processor unit 926. The display unit 932 may include one or more monitors that display patient information, such as diagnostic images for review, diagnosis, analysis, and treatment. The display unit 932 may automatically display data stored in the memory (not shown) or currently being acquired. This stored data may also be displayed with a graphical representation.

Moreover, the system 900 may include a feedback unit 934. The feedback unit 934 may be operatively coupled to the processor unit 926. Further, the feedback unit 934 may be operatively coupled to one or more electrical channels 906. The feedback unit 934 may be configured to provide feedback to the processor unit 926 regarding the resultant voltages at the electrodes 904. In one embodiment, the feedback unit 934 may be configured to communicate with the processor unit 926, electrical channel 906, or both. In particular, the feedback unit 934 may be configured to instruct the processor unit 926, the electrical channels 906, or both to exclude the contribution of the electrodes that are not properly coupled to the subject of interest. By way of example, in instances where one or more electrodes 904 are not coupled properly to the subject of interest, the feedback unit 934 may be configured to provide feedback to the processor unit 926 to reject the values, such as the resultant voltages and the contact impedances associated with that particular electrode 904. Upon receiving instructions from the feedback unit 934, the processor unit 926 may be configured to not provide a determined current pattern to the corresponding electrical channel 906.

Further, the system 900 may include one or more input devices 936 that are communicatively coupled to the processor unit 926. The input devices 936, for example, may include a keyboard, a mouse, a trackball, a joystick, a touch-activated screen, a light wand, a control panel, and/or an audio input device such as a microphone associated with corresponding speech recognition circuitry. The input devices 936 may also allow a user, such as a medical practitioner to input desirable information/instructions, such as, but not limited to, determined current patterns. In one embodiment, the input devices 936 may be used by the user to provide a number of iterations or conditions that need to be met for the iterative process to commence by applying determined current patterns and reconstructing an image may be allowed to run.

It should be noted that the various embodiments of the present specification may be implemented, for example, in connection with different types of soft-field tomography systems, such as the EIS, EIT, or ECT and related modalities.

Furthermore, the foregoing examples, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

Advantageously, the systems and methods described hereinabove are configured to maximize the ability to detect and quantify changes inside the body non-invasively by applying determined current patterns that maximize distinguishability. Typically, electrical impedance imaging systems and methods are highly sensitive to small perturbations; hence, the ability to compensate for undesirable change in the contact impedances aids in enhancing the quality of images. The various systems and methods for compensating at least in part for a change in contact impedance of one or more electrodes of the plurality of electrodes described hereinabove provides a framework for robust impedance imaging of a desired biological material. Moreover, the various systems and methods are automated, thereby circumventing the need for manual intervention.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method for impedance imaging of a subject of interest using a plurality of electrodes, comprising:
applying one or more determined current patterns to one or more electrodes of the plurality of electrodes;
measuring resultant voltage at at least one electrode of the one or more electrodes in response to the one or more determined current patterns, using mathematical decomposition;
estimating a change in a contact impedance for the at least one electrode of the one or more electrodes, wherein estimating the change in the contact impedance comprises determining a matrix of resistances corresponding to the one or more electrodes based on the measured resultant voltage, and wherein the matrix of resistances corresponding to the one or more electrodes comprises individual resistances of the one or more electrodes; and,
calculating a compensated voltage for the at least one electrode based on an estimated change in a corresponding contact impedance of an electrode of the one or more electrodes, wherein calculating the compensated voltage comprises using the estimated change in the contact impedance for the at least one electrode to adjust the measured resultant voltage at the at least one electrode.

2. The method for electrical impedance imaging of claim 1, comprising estimating a change in a contact impedance between a pair of electrodes of the plurality of electrodes.

3. The method for electrical impedance imaging of claim 1, comprising estimating a change in a contact impedance for at least one electrode of the one or more electrodes at two or more instants in time.

4. The method for electrical impedance imaging of claim 1, wherein calculating the compensated voltage for the at least one electrode comprises subtracting a portion of a voltage from the measured resultant voltage, and wherein the portion of the voltage corresponds to the estimated change in the corresponding contact impedance of the electrode.

5. The method for electrical impedance imaging of claim 1, further comprising reconstructing one or more images based on compensated voltages of the one or more electrodes.

6. The method for electrical impedance imaging of claim 1, comprising:
reconstructing an image of the subject of interest based on the one or more determined current patterns and a corresponding resultant voltage at each of the one or more electrodes;
providing the estimated change in the contact impedance of the at least one electrode of the one or more electrodes to a processor unit;
calculating a compensated voltage for each of the one or more electrodes; and
reconstructing another image of the subject of interest based on the one or more determined current patterns, the corresponding resultant voltage, and the compensated voltage for each of the one or more electrodes.

7. The method for electrical impedance imaging of claim 1, further comprising changing the one or more determined current patterns based on the estimated change in the contact impedance.

8. The method for electrical impedance imaging of claim 1, wherein the estimating the change in the contact impedance of the at least one electrode comprises:
calculating a resistance for the at least one electrode; and
modeling a change in the resistance of the at least one electrode to estimate the change in the contact impedance of the at least one electrode.

9. The method for electrical impedance imaging of claim 8, wherein the modeling comprises using series resistance-capacitance circuits or parallel resistance-capacitance circuits, or both.

10. The method for electrical impedance imaging of claim 1, further comprising filtering the estimated change in the contact impedance of the electrode, wherein filtering the estimated change in the contact impedance comprises:
eliminating a change in the contact impedance due to a physiological phenomenon;
eliminating an expected temporal signal, a spectral physiological signal, or a combination thereof from the estimated change in the contact impedance; and
retaining a desired change in the contact impedance due to an electrode-skin interface.

11. The method for electrical impedance imaging of claim 10, wherein the filtering comprises fitting one or more estimated changes in one or more contact impedances to a determined model.

12. The method for electrical impedance imaging of claim 1, further comprising measuring the resultant voltage before imaging and during imaging.

13. The method for electrical impedance imaging of claim 1, further comprising reconstructing one or more images in real-time using the compensated voltage for the at least one electrode.

14. The method for electrical impedance imaging of claim 1, wherein estimating the change in the contact impedance of the at least one electrode comprises using a change in one or more of an electrical conductivity, a permittivity, and a frequency of a current of one or more determined current patterns with respect to time corresponding to the at least one electrode.

15. The method for electrical impedance imaging of claim 1, calculating a compensated voltage for the at least one electrode comprises calculating the compensated voltage subsequent to the estimation of the change in the contact impedance and measurement of the resultant voltage at at least one electrode of the one or more electrodes.

16. The method for electrical impedance imaging of claim 1, wherein the contact impedance is determined based on the individual resistances and a resistance of a medium between the at least two electrodes.

17. A method for imaging a subject of interest using electrical impedance imaging, comprising:
 a) applying one or more determined current patterns to two or more electrodes of a plurality of electrodes;
 b) determining one or more resultant voltages at the two or more electrodes at two or more instants in time, using mathematical decomposition;
 c) estimating changes in contact impedances for the two or more electrodes at the two or more instants in time, wherein estimating the changes in the contact impedances comprises determining a matrix of resistances corresponding to the one or more electrodes based on the determined one or more resultant voltages, and wherein the matrix of resistances corresponding to the one or more electrodes comprises individual resistances of the one or more electrodes;
 d) if there is a change in a contact impedance for a given electrode between the two or more instants in time, calculating a compensated voltage for the given electrode based on the change in the contact impedance for the given electrode; and
 e) reconstructing an image based on the compensated voltage for each of the two or more electrodes.

18. The method of claim 17, comprising repeating steps a) to e) for each pair of electrodes of the plurality of electrodes at the two or more instants in time.

19. The method of claim 17, further comprising modifying the one or more determined current patterns based on compensated voltages for the two or more electrodes.

20. The method of claim 19, further comprising repeating steps a) to e) for each electrode of the plurality of electrodes using the modified current patterns.

\* \* \* \* \*